Figure 1:
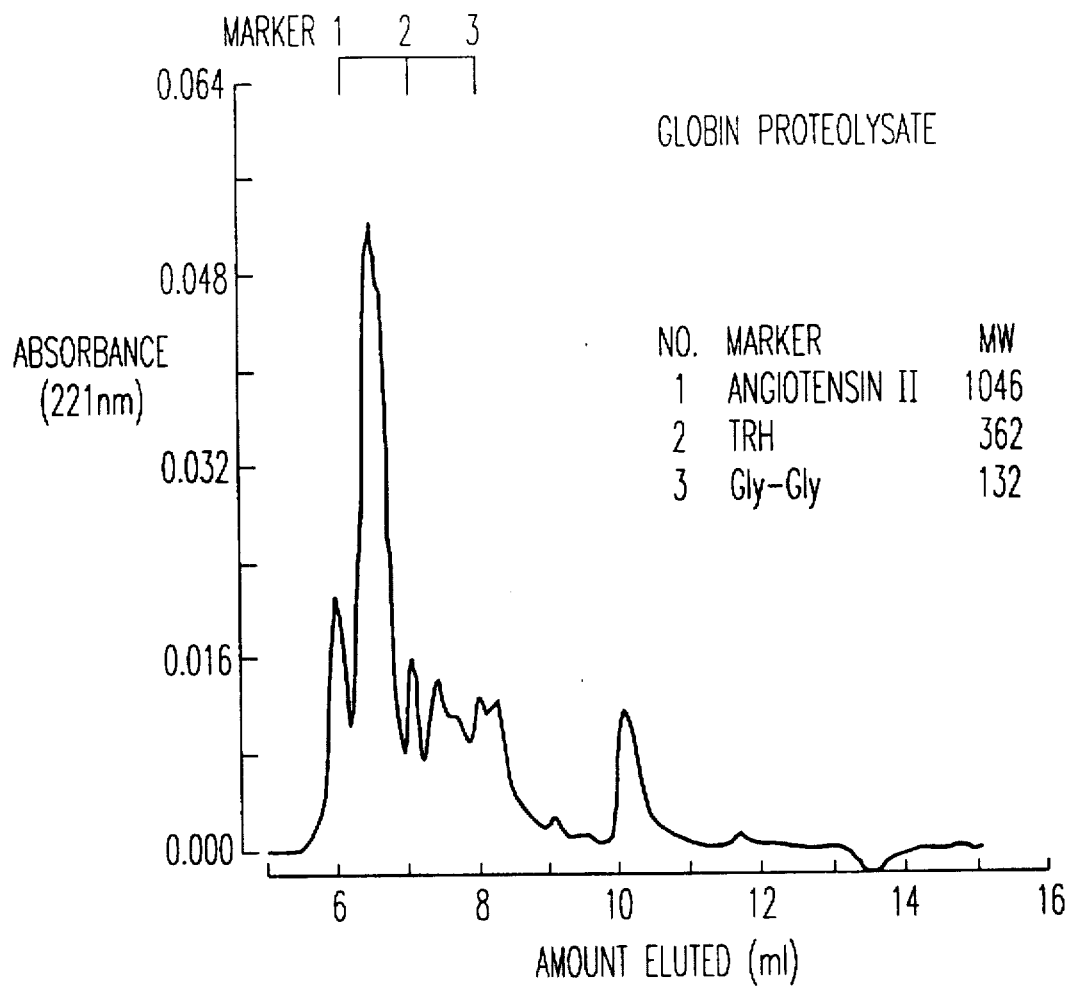

United States Patent [19]
Kagawa et al.

[11] Patent Number: 5,756,467
[45] Date of Patent: May 26, 1998

[54] ADIPOCYTE DIFFERENTIATION INHIBITING PEPTIDE AND ADIPOCYTE DIFFERENTIATION INHIBITING AGENT USING THE PEPTIDE AS ACTIVE COMPONENT THEREOF

[75] Inventors: Kyoichi Kagawa; Chizuko Fukuhama; Hisako Matsutaka; Toru Iguchi, all of Ikeda; Toyoo Nakamura, Ibaraki; Masahiro Numata, Ibaraki; Shigeaki Watanabe, Ibaraki, all of Japan

[73] Assignees: Itoham Foods Inc., Kobe; Hankyu-Kyoei Bussan Co., Ltd., Osaka, both of Japan

[21] Appl. No.: 525,515

[22] PCT Filed: Feb. 24, 1994

[86] PCT No.: PCT/JP94/00297

§ 371 Date: Sep. 25, 1995

§ 102(e) Date: Sep. 25, 1995

[87] PCT Pub. No.: WO94/21671

PCT Pub. Date: Sep. 29, 1994

[30] Foreign Application Priority Data

Mar. 24, 1993 [JP] Japan ................... 5-065643

[51] Int. Cl.$^6$ ................................................ A61K 38/00
[52] U.S. Cl. .................... 514/18; 530/331; 426/656; 435/71.1
[58] Field of Search ............... 530/331; 514/18; 426/656; 435/71.1

[56] References Cited

FOREIGN PATENT DOCUMENTS

| | | |
|---|---|---|
| 8930370 | 8/1989 | Australia . |
| 0 044 032 | 1/1982 | European Pat. Off. . |
| 0 420 979 | 4/1991 | European Pat. Off. . |
| 331298A | 2/1991 | Japan . |
| 3120224 | 5/1991 | Japan . |

OTHER PUBLICATIONS

Agricol. Biol. Chem., vol. 52, No. 1, pp. 95–98, Norio Ishibashi, et al., "Taste of Proline–Containing Peptides", 1988.

Boehlen et al., "Purification of peptides: an efficient procedure for the separation of peptides from amino acids and salt.", *Int. J. Pept. Protein Res.* (1980), 16(4), 306–10.

*Primary Examiner*—Cecilia J. Tsang
*Assistant Examiner*—C. Delacroix-Muirheid
*Attorney, Agent, or Firm*—Oblon, Spivak, McClelland, Maier & Neustadt, P.C.

[57] ABSTRACT

This invention aims to provide a peptide having an amino acid sequence of Val-Tyr-Pro or Val-Thr-Leu and having the ability to inhibit adipocyte differentiations, adipocyte differentiation inhibiting agent incorporating therein as an active component the peptide or a proteolysate characterized by containing not less than 0.1% by weight of the peptide, a specific health food, and a feed. This invention permits prevention and therapy of obesity and cardiovascular diseases attendant on obesity such as hypertension and arteriosclerosis in men and animals. It also allows improvement of the meat quality in domestic animals and culured fish.

34 Claims, 3 Drawing Sheets

ADIPOCYTE DIFFERENTIATION INHIBITING PEPTIDE AND ADIPOCYTE DIFFERENTIATION INHIBITING AGENT USING THE PEPTIDE AS ACTIVE COMPONENT THEREOF

TECHNICAL FIELD

This invention relates to a novel adipocyte differentiation inhibiting peptide, adipocyte differentiation inhibiting agent using the peptide as an active component thereof, a specific health food (so-called physiologically physiolosically functional food) possessing the function of inhibiting adipocyte differentiation, and an animal feed possessing the function of inhibiting adipocyte differentiation. It further relates to a specific health food (so-called physiolosically functional food) incorporating therein a proteolysate containing the adipocyte differentiation inhibiting peptide mentioned above, possessing the function of inhibiting adipocyte differentiation and an animal feed possessing the function of inhibiting adipocyte differentiation. This invention allows prevention and therapy of obesity of men or animals and cardiovascular diseases attendant on obesity such as hypertension and arteriosclerosis. It further permits improvement of the meat quality of domestic animals and cultured fish.

BACKGROUND ART

It is held that excessive ingestion of fat and carbohydrate induces obesity and hyperlipidemia and even develops hypertension and arteriosclerosis ultimately. The desirability of repressing the absorption of fat and carbohydrate and diminishing the accumulation of fat has, therefore, been finding enthusiastic recognition.

Infants, on exposure to excessive ingestion of nutrition, suffer increase of adipocytes and assume the state which may well be called potential obesity. By this reason, it has been reported that the repression of the increase of the number of adipocytes particularly in infants results directly in the prevention of the obesity and the cardiovascular diseases which may well be called complications of obesity in children and consequently in adults.

For the therapy of obesity and hyperlipidemia, such measures as limitation of meal, ingestion of diet food (such as, for example, fibers), and even administration of various medicines have been in vogue. The medicines now in popular use include dextran sulfate which enhances the lipoprotein lipase activity in blood, nicomol which inhibits absorption of lipid, especially cholesterol, and clofibrate and pravastatin which are agents for improving metabolism of lipid, for example.

Unfortunately, the limitation of meal is an agony for persons obliged to pursue this exercise and the administration of such medicines as mentioned above possibly entrains side effects.

The domestic animals and the cultured fish are now given enriched feed which is aimed at promoting growth. As a result, the domestic animals and the cultured fish have unduly high fat contents in their meat. The enriched feed, accordingly, compels the domestic animals and the cultured fish to suffer excessive intake of fat and degradation of the taste of their meats below the level meeting consumers' fancy.

Recently, an oligopeptide-containing substance developed by researchers including one of the inventors of the instant patent application has been already applied for patent (International Patent Disclosure W089/06970). A technique similar thereto is disclosed in JP-A-02-154,693.

In these patent publications, it is clearly remarked that certain species of oligopeptides are effective in improving metabolism of lipids.

The oligopeptide-containing substance disclosed in the patent application mentioned above is a mixture of hydrolysates of protein in composition. The amino acid sequence of the true active component of this substance, namely a peptide as an active component, is not demonstrated.

This fact implies that the peptide-containing substance has a too low purity to be utilized as a medicine. This substance permits no perfect quality control because the substance, when incorporated in food, cannot be easily quantified separately from the peptide inherent in the food.

Under the circumstances, the identification of the true active component, i.e. the peptide as an active component, of the peptide-containing substance under discussion is posed as a task.

This invention fulfills a task of isolating the peptide as the active component mentioned above, analyzing the amino acid sequence, providing adipocyte differentiation inhibiting agent having the peptide as an active component thereof, and providing adipocyte differentiation inhibiting agent containing as an active component thereof an oligopeptide-containing substance obtained from a specific protein.

DISCLOSURE OF THE INVENTION

The present inventors made a diligent study with a view to accomplishing the task mentioned above. They have consequently found that this task is attained by the following invention.

Specifically, this invention essentially realizes the following objects:

(1) A peptide having an amino acid sequence of Val-Tyr-Pro or Val-Thr-Leu and exhibiting an ability to inhibit adipocyte differentiation.

(2) A adipocyte differentiation inhibiting agent characterized by containing as an active component thereof the peptide set forth in (1) above.

(3) A specific health food characterized by containing as an active component thereof the adipocyte differentiation inhibiting peptide set forth in (1) above and endowed with the function of inhibiting adipocyte differentiation.

(4) A feed incorporating the adipocyte differentiation inhibiting peptide set forth in (1) above therein and endowed with the function of inhibiting adipocyte differentiation.

(5) A specific health food characterized by containing as an active component thereof a proteolysate characterized by containing not less than 0.1% by weight of the adipocyte differentiation inhibiting peptide set forth in (1) above and endowed with the function of inhibiting adipocyte differentiation.

(6) A feed incorporating therein a proteolysate characterized by containing not less than 0.1% by weight of the adipocyte differentiation inhibiting peptide set forth in (1) above.

Now, this invention will be described in detail below.

The peptides, Val-Tyr-Pro and Val-Thr-Leu, of the present invention can be isolated as refined from proteins which occur in the natural world. They can also be chemically synthesized directly by the known method. The peptides of this invention can be alternatively manufactured by preparing a oligonucleotide possessing a base sequence corresponding to the amino acid sequence mentioned above, inserting this oligonucleotide into an appropriate expression vector, and inducing expression of this peptides in an appropriate host.

A. Now, a procedure for isolating as refined the peptides from proteins occurring in the natural world will be described below.

As raw materials, animal proteins such as fish meat protein, fish flour, and globin and plant proteins such as wheat gluten and soy bean casein can be extensively used.

Globin proteins such as hemoglobin and myoglobin, among other proteins mentioned above, prove particularly advantageous in strongly manifesting an expected effect of inhibiting adipocyte differentiation.

The kinds of animals which are donors of these globin proteins are not particularly limited. The bloods of cow, hog, sheep, man, horse, etc. can be extensively used.

Then, the protein noted above must be hydrolyzed. The procedure for this hydrolysis conforms to the method which is disclosed in the specification of International Patent Disclosure W089/06970 mentioned above. The hydrolytic enzymes which can be effectively used herein include acid proteases, neutral proteases, and alkaline proteases, for example. They may be used either singly or in the form of a mixture of two or more members.

The conditions under which the globin protein is hydrolyzed will be described below.

A globin protein-containing substance is hydrolyzed by first dispersing this substance in water at a concentration in the range of from 5 to 30% by weight on solid basis, adjusting the resultant dispersion with an acid or an alkali to an optimum pH for a protease, adding the protease at once or gradually to the dispersion of the optimum pH value, and heating the mixture at a temperature in the range of from 20 to 70° C. for 3 to 48 hours thereby causing the enzyme to react with the substrate.

Then, a proteolysate having the effect of inhibiting adipocyte differentiation (hereinafter referred to as "hydrolysate of the inventions") is obtained by drying the resultant proteolysate or combining this proteolysate with a suitable amount of an extender such as carboxymethyl cellulose or dextrin and drying the resultant mixture until solidification.

This hydrolysate of the invention contains the peptide of this invention, Val-Tyr-Pro and/or Val-Thr-Leu, at a concentration of at least 0.1% by weight.

Subsequently, the proteolysate of this invention resulting from the treatment with the enzyme is purified. For this purification, any of the well-known methods for purification can be adopted.

To be specific, a fraction containing a peptide aimed at can be manufactured in a purified state by suitably combining the method using an ion-exchange resin, the method of ultrafiltration, the method of reversed-phase chromatography, etc.

The procedure of isolation remarked above does not always necessitate an operation by the method of using an ion-exchange resin or the method of ultrafiltration. From the viewpoint of exalting the degree of isolation and purification, however, this operation is advantageously incorporated in the procedure.

The isolation and purification is realized by combining the operation of the reversed-phase chromatography in an acid state and the operation of the reversed-phase chromatography in a neutral state. The protein content of the fraction can be determined by any of the well-known methods for determination of protein such as, for example, the ninhydrin method.

By identifying the amino acid sequence of the fraction separated as described above in accordance with the well-known method, the presence of the peptides of this invention, Val-Tyr-Pro and Val-Thr-Leu, in this fraction can be confirmed.

The peptide of this invention which originates in the fraction isolated as described above can be used as an active component for the fat differentiation inhibiting agent of this invention.

The fraction isolated as described above can be otherwise used directly as an active component for the agent of the present invention for inhibiting the adipocytes differentiation.

The peptide of this invention can be chemically synthesized by the well-known methods of peptide synthesis. AS concrete examples of the method for synthesis, azide method, acid chloride method, acid anhydride method, mixed acid anhydride method, DCC method, activated ester method, carbodiimidazole method, redox method, and DCC-additive (HOMB, HOBt, HOSu) method ["The Peptide", Vol. 1 (1966), written by Schreder & Luhke and published by Academic Press, New York, USA or "Synthesis of Peptides", written by Izumitani et al. and published by Maruzen Co., Ltd. (1975)] may be cited.

The method for synthesis of a peptide mentioned above can be implemented in the form of solid phase synthesis or liquid phase synthesis.

Further in the operation of the method for synthesis of a peptide mentioned above, amino acids possessing a side-chain functional group such as, for example, tyrosine and threonine, preferably have the relevant side-chain functional groups protected during the course of synthesis. For the purpose of this protection, the well-known protective groups such as, for example, benzyloxycarbonyl group (Cbz-), t-butoxycarbonyl group (Boc-), and benzyl group (Bz-) can be used.

Incidentally, the protective group can be removed by the well-known method in the process of synthesis of the peptide of this invention.

B. Adipocyte differentiation inhibiting agent can be manufactured using the peptide of this invention as an active component thereof.

As a carrier for the differentiation inhibiting agent, any of such excipients or diluents as filler, extender, binder, moistening agent, disintegrating agent, and surface active agent which are commonly used in the manufacture of a chemical agent in a form suitable for actual use can be used. The form of the composition of the chemical agent has no particular restriction except for the requirement that it be capable of effectively containing the peptide of this invention. Concrete examples of the form of the composition include solids such as tablets, powder, granules, and pills and solutions, suspensions, and emulsions which are suitable for administration by injection. Optionally, the chemical agent may be manufactured in the form of a dry preparation which can be liquefied prior to use by the addition of a suitable carrier. All these chemical agents can be manufactured by the ordinary methods known to the art.

The dosage of the adipocyte differentiation inhibiting agent is suitably selected in accordance with the method of administration of the agent, the form of administration, the symptom of a patient requiring the administration, and the like.

Generally, the chemical agent is preferably prepared in a form containing the peptide of this invention in a concentration in the approximate range of from 0.001 to 80% by weight and administered at a dosage containing the peptide of this invention at a concentration in the approximate range of from 1 mg to 100 mg per adult per day. This administration is not always required to be made once daily but may be made as split into three or four doses per day.

The medicines of the various forms mentioned above are administered through paths suitable for their particular forms. Those of the forms fit for injection, for example, are administered by intravenous injection, intramuscular injection, hypodermic injection, intradermal injection, and intra-abdominal injection and those of a solid form are administered orally.

C. A specific health food (so-called physiolosically functional food) can be manufactured using as an active component thereof the peptide of this invention or the hydrolysate of this invention (hereinafter referred to as "peptide of the invention"). The peptide or the hydrolysate can be used as additive for ordinary food.

The kinds of the food mentioned above are not specifically restricted. Concrete examples of the food to which the peptide of this invention can be added include milk, pudding, curry, hash, stew, meat sauce, ham, cake, and chocolate.

Milk, among other foods mentioned above, proves particularly advantageous in respect that it enables the peptide of this invention which is not easily ingested directly by children on account of gustatory sense to be easily ingested. Further, the addition of the peptide of the invention to such foods as cakes and chocolate which inherently promote obesity proves advantageous in preventing the obesity due to the ingestion of such foods.

The amount of the peptide of the invention to be incorporated in the food mentioned above is suitably selected in accordance with the kind of food, the purpose of addition, the effect expected to be produced by the ingestion of the food, and the like.

Generally, the peptide of the invention is preferably incorporated in the food in such an amount that the food permits the intake of this peptide in an amount in the approximate range of from 0.1 mg to 4 mg per meal.

D. A feed having an ability to inhibit adipocyte differentiation can be prepared by adding the peptide of the invention to feed.

For addition to feed, the peptide of the invention does not discriminate between the feed for such domestic animals as cows, hogs, and chickens and the feed for such cultured fish as sea breams and young yellowtails.

The amount of the peptide of the invention for addition to the feed is suitably selected in accordance with the kind of feed, the effect expected to be produced by the ingestion of the feed, and the like.

Generally, the peptide of the invention is preferably added to the feed in such an amount that the feed contains the peptide at a concentration in the range of from 0.1 to 4% by weight.

EXAMPLES:

Now, this invention will be described more specifically below with reference to examples. It should be noted that the technical scope of the present invention is not limited by these examples.

Example 1

Search for proteolysate having an action of inhibiting adipocyte differentiation Globin and wheat gluten were compared as protein sources capable of containing adipocyte differentiation inhibiting peptide. The test was carried out using mice of high-fat obesity and mice of high-sugar obesity as models of dietary obesity. The high-fat obesity was developed by allowing the mice to ingest freely 50% fat feed incorporating lard therein at a rate of 50 w/w % for two weeks and the high-sugar obesity by allowing the mice to ingest freely drinking water containing sucrose solution at a rate of 30 w/v % besides ordinary feed. The groups of mice tested for high-fat obesity were allowed to ingest freely the feeds severally having 4% of globin proteolysate, 8% of globin proteolysate, 2% of globin proteolysate+2% gluten proteolysate, and 4% of globin proteolysate+4% gluten proteolysate incorporated in 50% fat feed. In contrast, the groups of mice tested for high-sugar obesity were allowed to ingest freely the feeds severally having 2% of globin proteolysate, 4% of globin proteolysate, 1% of globin proteolysate+1% of gluten hydrolyzate, and 2% of globin proteolysate+2% of gluten proteolysate incorporated in ordinary feed besides 30% sucrose solution. The results are shown in Table 1.

In the test for high-fat obesity, the control group of 50% fat showed an increase of 190% or to about twice as high in the weight of the epididymal adipose tissue as compared with the control group of ordinary feed, accompanied by an increase of 50% in the number of tissue cells and an enlargement of 28% in the cell size. The increases in the weight of adipose tissue and the cell number and the enlargement of the cell size were noticeably repressed in the group exclusively ingesting globin proteolysate and the decrease of the cell number was particularly prominent in this group as compared with the group having wheat gluten proteolysate substituted for one half of the protein digestion product.

Similarly, in the test for high-sugar obesity, the globin proteolysate showed a stronger trend to repress the increase in the number of adipocytes than the wheat gluten proteolysate.

From these results, it is noted that the globin proteolysate excels in the action to inhibit adipocyte differentiation and it is suspected that it has a high adipocyte differentiation inhibiting peptide content.

The data justify a conclusion that globin proteins form preferable principles without reference particularly to protein sources.

TABLE 1

Effect of proteolysate on increase of adipocytes

| Treatment | Cell number[1] | Cell size[2] | Tissue weight[3] | Body weight gain[4] |
|---|---|---|---|---|
| Normal meal | 17 | 7.5 | 0.89 | 22.8 |
| 50% fat meal | 25 | 9.6 | 1.70 | 25.0 |
| +4% Globin proteolysate | 16 | 9.4 | 1.08 | 22.3 |
| +8% Globin proteolysate | 15 | 9.9 | 1.05 | 22.3 |
| +2% Globin proteolysate + 2% gluten proteolysate | 20 | 8.1 | 1.11 | 20.2 |
| +4% Globin proteolysate + 4% gluten proteolysate | 19 | 8.5 | 1.14 | 21.7 |
| Normal meal | 15 | 9.5 | 0.98 | 18.0 |
| 50% Sucrose solution | 20 | 12.9 | 1.82 | 27.6 |
| +2% Globin proteolysate | 14 | 9.4 | 1.46 | 21.9 |
| +4% Globin proteolysate | 16 | 9.9 | 1.28 | 21.7 |
| +1% Globin proteolysate + 1% gluten proteolysate | 19 | 8.1 | 1.44 | 20.8 |
| +2% Globin proteolysate + 2% gluten proteolysate | 19 | 8.5 | 1.37 | 23.6 |

[1] $\times 10^6$ cells/adipose tissue
[2] Fat mg/μg of DNA
[3] Weight (g) of adipose tissue surrounding epididymis
[4] Increase in body weight (g)

Example 2
Production of globin proteolysate

A method for the production of globin proteolysate using bovine red blood corpuscles will be described in detail below. The molecular weight distribution was determined by the method of gel chromatography (FIG. 1).

This chromatography was carried out under the following conditions.

Apparatus: High-performance liquid chromatography, model LC-6A, Shimadzu Corp.
Column: Polyhydroxyethyl A., 5 μm 9.4×200 mm, Poly LC Inc.
Solvent for elution: 50 mM formic acid
Flow rate: 0.5 ml/min.
Detection: Ultraviolet absorption (221 nm)

A thorough hemolysate obtained by adding 250 liters of water to 100 kg of fresh bovine red blood corpuscles was adjusted to pH 2.8 by addition of phosphoric acid and then left reacting with $2.6 \times 10^7$ units of acid protease of Aspergillus niger added thereto at 50° C. for three hours.

After the reaction, the reaction solution was heated at 80° C. for 30 minutes to stop the reaction proceeding therein, then adjusted to pH 6.5 by addition of the suspension of calcium hydroxide in water, combined with 10 kg of diatomaceous earth, and filtered by the use of a filter press. The resultant filtrate was spray dried to obtain 23 kg of powder.

Example 3
Method for fractional purification of adipocyte differentiation inhibiting peptide The peptide of the invention was obtained by following the procedure consisting of: 1. ion exchange, 2. ultrafiltration, 3. separation by reversed-phase column chromatography in acidic state, and 4. separation by reversed-phase chromatography in neutral state, which are indicated below.

The ratios of recovery obtained by the use of these steps are shown in Table 2. The amounts of proteins were determined by the ninhydrin method.

TABLE 2

Ratio of recovery of adipocyte differentiation inhibiting peptide from globin proteolysate

| Fraction | Protein weight (g) | Yield (%) | Method of determination |
|---|---|---|---|
| Globin proteolysate | 13.7 | 100 | Ninhydrin method after acid hydrolysis |
| Ion exchange + ultrafiltration | 4.24 | 30.9 | Same as above |
| Reversed-phase (acid) chromatography Reversed-phase (neutral) chromatography | 0.039 | 0.28 | Amino acid analysis after acid hydrolysis |
| (1) Val-Thr-Leu (fraction B) | 0.009 | 0.06 | Same as above |
| (2) Val-Tyr-Pro (fraction C) | 0.006 | 0.04 | Same as above |

1. Ion exchange

An aqueous 10 w/v % globin proteolysate solution and a weakly acidic cation-exchange resin (Amberlite IRC50, H⁺form, produced by Japan Organo Co., Ltd.) added thereto were stirred for one hour to induce adsorption and obtain an unadsorbed fraction.

2. Ultrafiltration

The unadsorbed fraction obtained by the ion-exchange treatment was subjected to ultrafiltration by the use of a stirring ultrafiltration device (UHP 90K produced by Advantek Co., Ltd.) and an ultrafiltration membrane (fraction molecular weight 1000, UII 1, Advantec Co., Ltd.), followed by collection of the filtrate.

Figure 2:
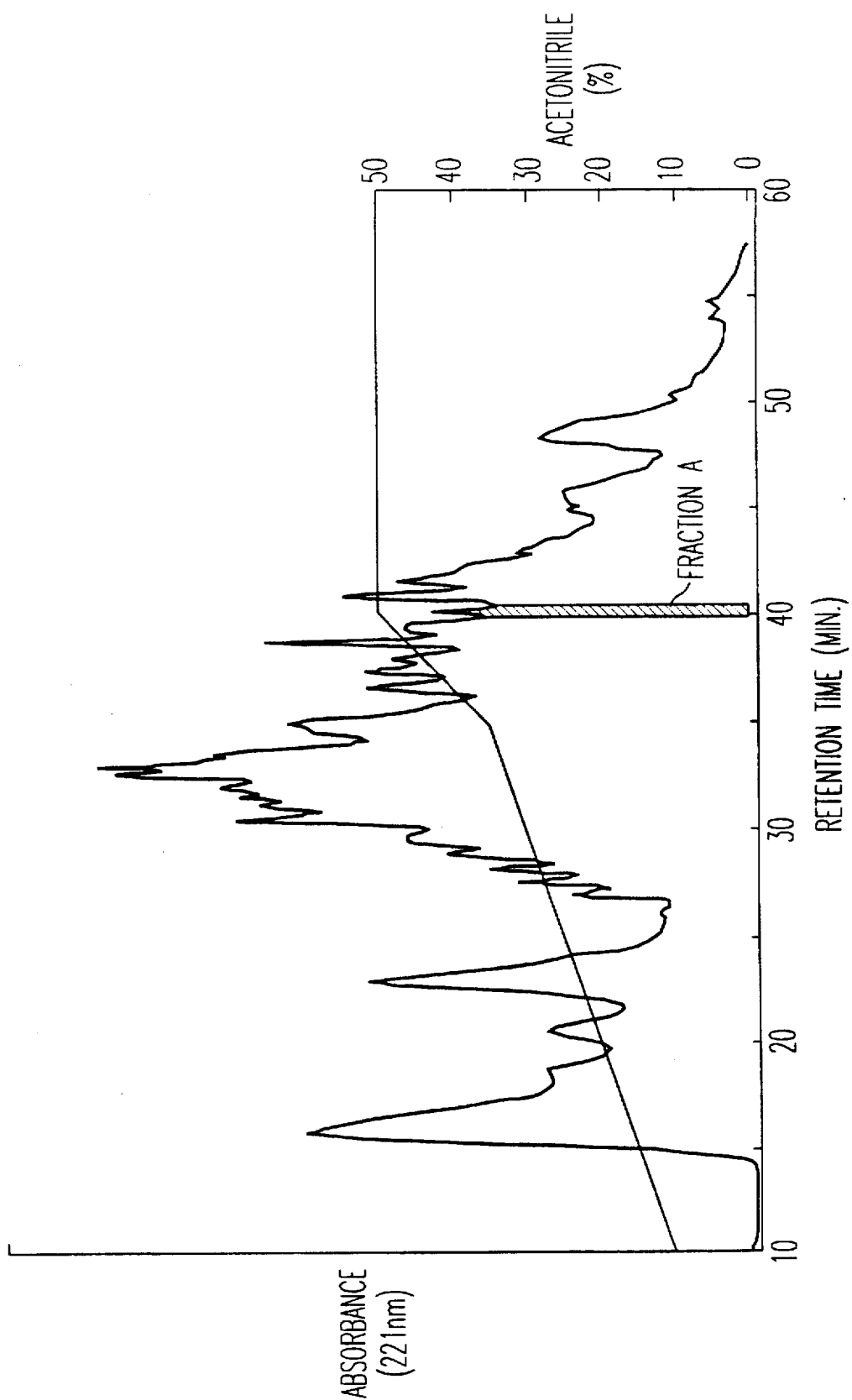

3. Reversed-phase (acid) chromatography (FIG. 2)

Figure 3:
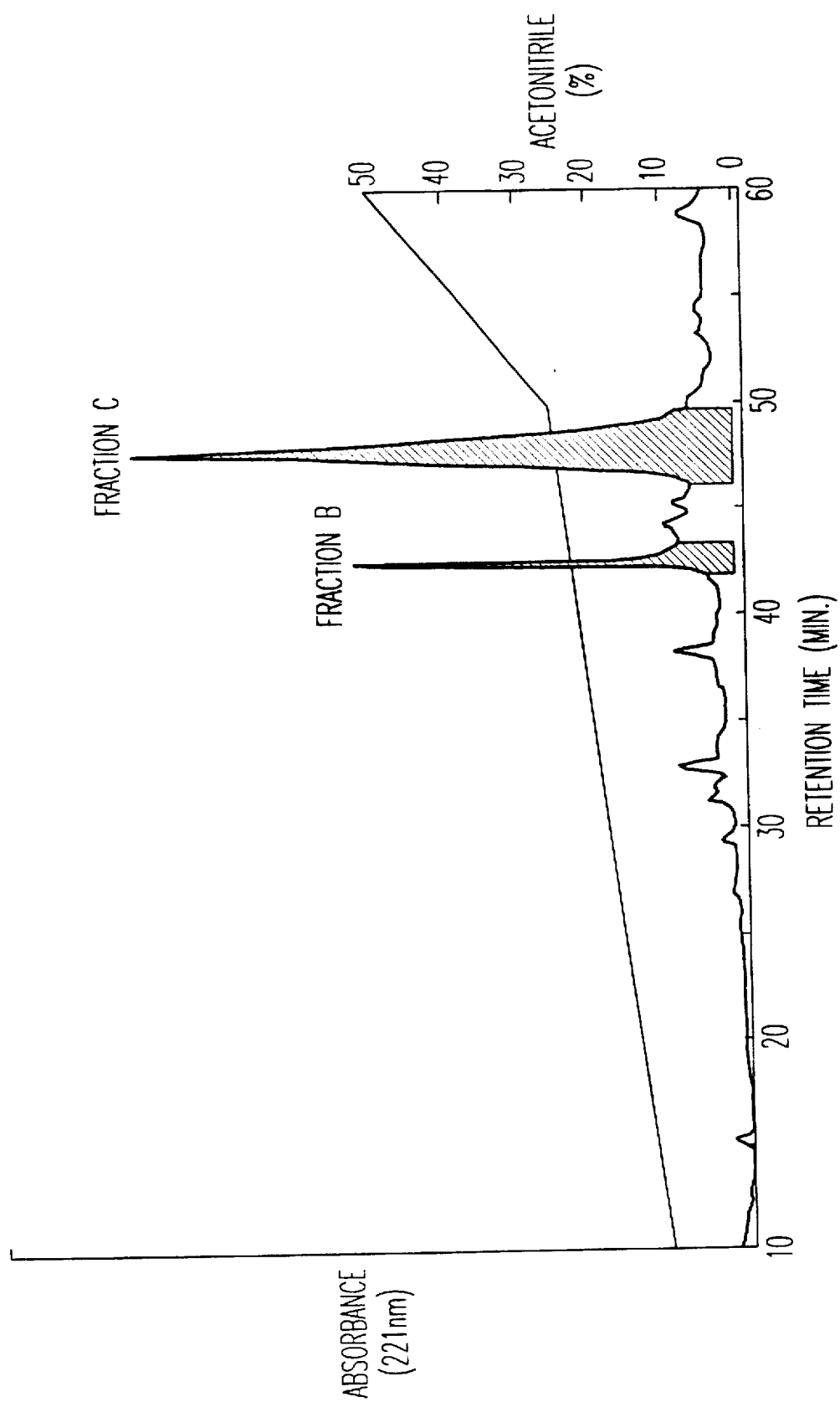

Apparatus: High-performance liquid chromatography (Model LC1-10A, Shimadzu Corp.)
Column: SuperPac Pep-S, 15 Êm, 22.5×250 mm, Pharmacia Ltd.
Solvent for elution: Aqueous acetonitrile solution containing 0.1% trifluoroacetic acid, with the concentration of acetonitrile linearly graded from 2% through 35% at a rate of 1%/minute.
Flow rate: 5 ml/minute
Temperature: 50° C.
Detection: 220 nm Time for fractionation (fraction A): 39.9 to 40.4 minutes 4. Reversed-phase (neutral) chromatography (FIG. 3)

Apparatus: High-performance liquid chromatography (Model LC-10A, Shimadzu Corp.)
Column: SuperPac Pep-S, 15 μm, 22.5×250 mm, Pharmacia Ltd.
Solvent for elution: Aqueous acetonitrile solution containing 20 mM ammonium acetate buffer (pH 6.5), with the concentration of acetonitrile linearly graded from 0% through 25% at a rate of 0.5%/minute.
Flow rate: 5 ml/minute
Temperature: 50° C.
Detection: Ultraviolet absorption (220 nm)
Time for fractionation:

(1) Fraction B—41.7 to 43.2 minutes (Val-Thr-Leu)

(2) Fraction C—45.8 to 51.0 minutes (Val-Tyr-Pro)

Example 4
Quantification of adipocyte differentiation inhibiting peptide

The quantification of the peptide fraction having adipocyte differentiation inhibiting activity in the globin proteolysate obtained in Example 2 was carried out by following the method for purification of available peptide shown in Example 3, with necessary modifications.

Acid hydrolysis

In a test tube, 1 ml of hydrochloric acid placed in a final concentration of 6N in 3 to 5 mg of protein was heated at 110° C. for 22 hours under normal pressure in the case of the ninhydrin method or under a reduced pressure in the case of the amino acid analysis.

Ninhydrin method

A hydrolyzed sample was adjusted to pH 5.0 by addition of sodium hydroxide and left reacting with a ninhydrin reagent containing 0.2M citric acid buffer (pH 5.0) at 100° C. for 15 minutes. The resultant reaction solution was tested for absorbance at 570 nm. Separately, the ninhydrin reaction was carried out on aqueous L-leucine solutions (0.75, 150, 225, and 300 n.moles/ml) as standard solutions. A calibration curve was prepared by plotting the absorbances obtained by the ninhydrin reaction. The amounts of amino group of the sample L-leucine were calculated based on the calibration curve.

Peptide map

Apparatus: High-performance liquid chromatography (Model LC-6A, Shimadzu Corp.)
Column: Shim-pack ISC-07/S1504 Na, 7 μm, 4.0×150 mm, Shimadzu Corp.
Solvent for elution: Amino acid mobile phase kit (Na form), Shimadzu Corp.
Flow rate: 0.3 ml/minute
Temperature: 55° C.

Reaction solution 1: Analysis kit OPA reagent, Shimadzu Corp.

Detection: Fluorescent absorption (Ex 348 nm, Em 450 nm)

Standard solution

Eighteen amino acid mixed standard solutions of H form (produced by Wako Pure Chemical Industries Ltd.) were diluted with 0.2M citric acid buffer (pH 2.20) to 25 times the original volume. The diluted solutions were injected at a dose of 10 µl (containing 1 nmoles of each amino acid/10 µl).

Sample solution

The solution resulting from the acid hydrolysis was concentrated to dryness by the use of a rotary evaporator and then dried under a reduced pressure for not less than 12 hours until thorough removal of hydrochloric acid. Then, the dry sample was dissolved in 0.2M citric acid buffer (pH 2.20) until the amino acid content decreased to a level of about 100 nmoles/ml. A filtrate obtained through a filter 0.45 µm in pore size was injected at a dose of 10 µl. The quantification of amino acid and the calculation of the peak area were effected by the analysis with a Chromatopack, C-R4A (produced by Shimadzu Corp.). The amount of amino acid was calculated by comparing the peak area of the sample solution with that of the standard solution. The amino acid composition was calculated by finding the ratios of the amounts of amino acids to the total of the amino acid contents found as above.

The results are shown in the form of yields in Table 2 given above.

Example 5

Preparation of H-Val-Thr-Leu-OH by chemical synthesis

A H-Val-Thr-Leu-OH was synthesized by peptide synthesizer (SAM 2, Blosearch Corp.) in accordance with its protocol. To be specific, 2 g of acyloxymethyl resin having 0.3 m mole of the third protected amino acid (Boc-Leu-OH) bound with per g of the resin was set in the reaction vessel of the synthesizer mentioned above and deblocked with the solution containing 45 v/v % trifluoroacetic acid (TFA), 2.5 v/v % anisole, and 52.5 v/v % of methylene chloride (DCM) for 25 minutes to remove Boc group. The resin was rinced with DCM, then neutralized with DCM containing 10v/v % diisopropyl ethylene amine, and further rinced with DCM. Subsequently, it was reacted in a mixed solution of dimethyl formamide (DMF) and 20 ml of DCM containing 4.0 m mole of Boc-Thr-OH and diisopropyl carbodiimide (each 6.7 times equivalent) at room temperature for two hours. Thereafter, it was rinced sequentially with DMF and DCM to obtain a Boc-Thr(Bz)-Leu-PAM resin.

It was then coupled with Boc-Val-OH by following the procedure described above.

The protected peptide resin resulting from the coupling mentioned above was reacted in anhydrous hydrogen fluoride containing 10 v/v % anisole at 0° C. for one hour, removed hydrogen fluoride by distillation, and rinced with ethyl ether. From the obtained mixture of peptide and resin, the peptide was extracted with 50% acetic acid. The extracted peptide was lyophilyzed to obtain about 250 mg of crude peptide.

The crude peptide was dissolved in 0.1% water, subjected to an octadecyl silica (ODS) column (Cosmosil $5C_{18}$, 250× 20 mm: Nakaraitesuku Co.) and with eluted 0.1% TFA/water in a linear gradient to 0.1% TFA/acetonitrile (20 to 70%/50 minutes, 10 ml/minute). The desired peptide was eluted at about 50% of acetonitrile .

Example 6

Preparation of food containing the peptide of the invention (1) <1> A powder milk having an ability to inhibit adipocyte differentiation was prepared by adding 1 g of the globin protein-containing substance obtained in Example 2 to 100 g of powder milk for infants.

<2> A powder milk having an ability to inhibit adipocyte differentiation was prepared by adding 0.1 g of the H-Val-Thr-Leu-OH synthesized in Example 5 to 100 g of powder milk for infants.

(2) <1> A chocolate having an ability to inhibit adipocyte differentiation was prepared by adding 5 g of the globin protein-containing substance obtained in Example 2 to 100 g of chocolate.

<2> A chocolate having an ability to inhibit adipocyte differentiation was prepared by adding 0.5 g of the H-Val(-Tyr-Pro-OH synthesized by the same method as in Example 5 to 100 g of chocolate.

Example 7

Preparation of feed containing the peptide of the invention

A feed for cultured fish having an ability to inhibit adipocyte differentiation was prepared by separately adding 10% by weight of the globin protein-containing substance obtained in Example 2 and 1% by weight of the H-Val-Thr-Leu-OH synthesized in Example 5 to 10% by weight of a premix incorporating vitamins, minerals, etc. therein and adding the premix at a ratio of 10% to the commercially available feed for cultured fish.

[Test 1] Effect of the globin proteolysate (GD) and the fraction A separated from the GD by the reversed-phase HPLC (FIG. 2) on preadipocyte (in vitro)

(1) Treatment before induction of differentiation

Swiss mouse 3T3-L1 cells were inoculated at a density of about $3 \times 10^4$ cells/ml to a cell culturing dish. A Dulbecco modified Eagle culture medium (DMEM) containing bovine fetal blood serum incorporated therein at a concentration of 10% was used as the culture medium. The culture was invariably carried out in an ambience of 5% $CO_2$ and 95% of air at 37° C.

After a monolayer of cells was formed, the cell layer surface was washed with a phosphate buffer physiological salt solution (PBS). In the presence of culture media containing the CD and the fraction A respectively at concentration of 0, 2, 4, and 8 mg/ml and at concentration of 0, 20, 40, and 80 µg/ml, the cell layer was cultured. Then, the cell layer surface was washed with PBS and the cell layer was cultured for two days in the presence of a culture medium incorporating therein the differentiation inducing substance (0.25 µM of dexamethasone, 0.5 mm of a-methyl-3-isobutyl xanthine, and 10 µg/ml insulin).

Subsequently, the cell layer was deprived of the culture medium containing the differentiation-inducing substance. The cell layer surface was washed likewise with PBS and the cell layer was cultured for about one week in the presence of a culture medium incorporating insulin therein at a concentration of 10 µg/ml.

The effect of the fraction A on the adipocyte differentiation was rated by determining the glycerol-3-phosphate dehydrogenase activity (GPDH) by the well-known method as a marker enzyme.

(2) Treatment after induction of differentiation

Swiss mouse 3T3-L1 cells were cultured by the same method as in (1) mentioned above and then tested for GPDH activity, providing that the culture medium containing insulin at a concentration of 10 µg/ml was added to the GD and the fraction A after the removal of the culture medium containing the differentiation inducing substance.

From Table 3 showing the results of the tests described above, it is clearly remarked that the GD and the fraction A were enabled by the treatment before and after the induction of differentiation to manifest a conspicuous action to inhibit the GPDH activity, depending on the peptide concentration and that these components were effective in inhibiting the adipocyte differentiations.

TABLE 3

Effect of GD and fraction A on adipocyte differentiation (in vitro)

| Peptide (mg/ml) | | Treatment before induction of differentiation (48 hours' treatment before induction) | | Treatment after induction of differentiation (48 hours' treatment after induction) | |
|---|---|---|---|---|---|
| | | GDPH activity (mU/mg protein) | Inhibition (%) | GDPH activity (mU/mg protein) | Inhibition (%) |
| GD | 0 | 514.6 ± 95.1 | — | 747.1 ± 28.9 | — |
| | 2 | 96.1 ± 18.9 | 81.3 | 599.6 ± 21.0 | 19.7 |
| | 4 | 7.8 ± 2.8 | 98.5 | 343.5 ± 64.4 | 54.0 |
| | 8 | 6.9 ± 1.9 | 98.6 | 16.2 ± 4.4 | 97.8 |
| Fraction A | 0 | 514.6 ± 95.1 | — | 747.1 ± 28.9 | — |
| | 20 | 87.3 ± 12.5 | 83.0 | 413.7 ± 31.2 | 44.6 |
| | 40 | 7.8 ± 3.1 | 98.5 | 318.5 ± 25.7 | 57.4 |
| | 80 | 6.7 ± 1.8 | 98.7 | 13.6 ± 2.7 | 98.2 |

[Test 2] Differentiation inhibiting effect of adipocyte differentiation inhibiting peptide (chemical synthesis product) on preadipocytes (in vitro)

The effects of the chemically synthesized H-Val-Thr-Leu-OH and the H-Val-Tyr-Pro-OH obtained by the same method as in Example 5 on Swiss mouse 3T3-L1 cells in were investigated by the same method as in Example 5. The concentrations of the relevant peptides in culture media were invariably 0, 0.2, 0.4, and 0.8 µg/ml.

From Table 4 showing the results of the tests described above, it is clearly remarked that the H-Val-Thr-Leu-OH and the H-Val-Tyr-Pro-OH were enabled by the treatment before and after the induction of differentiation to manifest a conspicuous action to inhibit the GPDH activity, depending on the peptide concentration and that these components were effective in inhibiting the adipocyte differentiations.

TABLE 4

Differentiation inhibiting effect of adipocyte differentiation inhibiting peptide (chemical synthetic product) on preadipocyte

| Peptide (mg/ml) | | Treatment before induction of differentiation (48 hours' treatment before induction) | | Treatment after induction of differentiation (48 hours' treatment after induction) | |
|---|---|---|---|---|---|
| | | GDPH activity (mU/mg protein) | Ratio of Inhibition (%) | GDPH activity (mU/mg protein) | Ratio of Inhibition (%) |
| (1)* | 0 | 571.3 ± 73.8 | — | 717.8 ± 45.6 | — |
| | 0.2 | 102.5 ± 19.6 | 82.1 | 463.2 ± 29.7 | 35.5 |
| | 0.4 | 8.1 ± 1.6 | 98.6 | 281.1 ± 19.6 | 60.8 |
| | 0.8 | 6.3 ± 1.9 | 98.9 | 13.8 ± 5.4 | 98.1 |
| (2)* | 0 | 571.3 ± 73.8 | — | 717.8 ± 45.6 | — |
| | 0.2 | 106.7 ± 28.1 | 83.0 | 412.6 ± 20.3 | 42.5 |

TABLE 4-continued

Differentiation inhibiting effect of adipocyte differentiation inhibiting peptide (chemical synthetic product) on preadipocyte

| Peptide (mg/ml) | Treatment before induction of differentiation (48 hours' treatment before induction) | | Treatment after induction of differentiation (48 hours' treatment after induction) | |
|---|---|---|---|---|
| | GDPH activity (mU/mg protein) | Ratio of Inhibition (%) | GDPH activity (mU/mg protein) | Ratio of Inhibition (%) |
| 0.4 | 10.6 ± 2.3 | 98.5 | 197.3 ± 27.5 | 72.5 |
| 0.8 | 7.8 ± 1.5 | 98.7 | 14.7 ± 2.7 | 98.0 |

*(1): H-Val-Thr-Leu-OH,
*(2): H-Val-Tyr-Pro-H

[Test 3] Effect of adipocyte differentiation inhibiting peptide (chemical synthesis product) (in vivo)

The two adipocyte differentiation inhibiting peptides of the invention, Val-Thr-Leu and Val-Tyr-Pro, synthesized by the method shown in Example 5 were tested for effect on increase of adipocytes (in vivo). The test was performed by the same method as in Test 1 using globin proteolysate.

It is clearly remarked from Table 5 showing the results of the test mentioned above that the two adipocyte differentiation inhibiting peptides, when added in such a small amount as 20 ppm, invariably decreased the cell number in the subcutaneous adipose tissue, epididymal adipose tissue, and the retroperitoneal adipose tissue. These results practically equal the results of the in vitro test using the 3T3-L1 cells of mouse.

TABLE 5

Effect of adipocyte differentiation inhibiting synthetic peptide on increase of cell number in murine adipose tissue

| Treatment | Subcutaneous adipose tissue | Epididymal adipose tissue | Retroperitoneal adipose tissue |
|---|---|---|---|
| Normal meal | 99* | 68 | 20 |
| 50% fat meal | 228 | 124 | 41 |
| +Val-Thr-Leu 20 ppm | 102 | 88 | 23 |
| +Val-Tyr-Pro 20 ppm | 125 | 102 | 27 |

*Number of adipocytes (average ± standard error, DNA µg/adipose tissue)

[Test 4] Effect of globin proteolysate on adipocyte differentiations (in vivo)

A globin proteolysate which contained the peptide of the invention in a required amount was tested in vivo for the effect thereof on the number of adipocytes in adipose tissue.

When male rats (species Wistar) were allowed to ingest freely a feed having the fat content thereof increased to 10%, a level of the fat content twice as high as that in ordinary feed, by addition of cocoa for four weeks, the cell number in the epididymal adipose tissue was found to be 138×10⁶, representing an increase of 22% as compared with the number, 113×10⁶, found in the group of rats ingesting ordinary feed (Table 6). When the feed having the fat content of 10% was made to incorporate the globin proteolysate therein in a concentration of 1 w/w %, the number of adipocytes was repressed to 119×10⁶, a level practically equal the number found in the rats ingesting ordinary feed. These results were similarly obtained in the cell tissue in the retroperitoneal adipose tissue, suggesting that the globin proteolysate and the wheat gluten proteolysate repressed the increase of the number of adipocytes due to the excessive ingestion of fat.

TABLE 6

Effect of proteolysate on increase of number of adipocytes in rat

| Treatment | Number of adipocytes[1] | Cell size[2] | Tissue weight[3] |
|---|---|---|---|
| Epididymal adipose tissue | | | |
| ordinary feed | 113 | 6.6 | 5.3 |
| 10% fat | 130 | 9.6 | 8.7 |
| + proteolysate | 119 | 10.4 | 8.6 |
| Retroperitoneal adipose tissue | | | |
| Ordinary feed | 77 | 7.2 | 3.9 |
| 10% fat | 97 | 9.4 | 6.4 |
| + Proteolysate | 79 | 11.5 | 6.4 |

[1] ×10$^6$ cells/adipose tissue
[2] fat mg/μg DNA
[3] Tissue weight (5)

Then, mice were allowed to ingest freely 50% fat feed and then tested for weight of adipose tissue and cell number. The results are shown in Table 7.

The ingestion of 50% fat feed invariably resulted in an increase of any of the adipose tissues to a level of not less than twice the level found in the ingestion of ordinary feed and brought about a proportionate increase in the cell number in the tissue. When the 50% fat feed was made to incorporate the globin proteolysate therein at a concentration of 2 to 12 w/w %, the increase of weight and the cell number were both repressed, depending on the dose.

TABLE 7

Effect of globin proteolysate on increase of adipose tissue

| Treatment | Subcutaneous adipose tissue | Epididymal adipose tissue | Retroperiton eal adipose tissue |
|---|---|---|---|
| Ordinary feed | 1.16 ± 1.41 | 0.83 ± .07 | 0.22 ± .03 |
| | 105 ± 132 | 79 ± 13 | 17 ± 3 |
| 50% fat feed | 3.68 ± .53 | 2.07 ± .24 | 0.54 ± .06 |
| | 213 ± 26 | 134 ± 15 | 34 ± 5 |
| +2% globin proteolysate | 2.77 ± .17 | 1.72 ± .09 | 0.42 ± .02 |
| | 143 ± 6** | 106 ± 5 | 29 ± 1 |
| +4% globin proteolysate | 2.74 ± .27 | 1.66 ± .22 | 0.45 ± .02 |
| | 133 ± 14** | 98 ± 12 | 34 ± 4 |
| +8% globin proteolysate | 2.41 ± .18* | 1.37 ± .08** | 0.40 ± .06** |
| | 131 ± 8** | 95 ± 9** | 27 ± 3 |
| +12% globin proteolysate | 1.96 ± .10** | 1.24 ± .11** | 0.36 ± .03** |
| | 103 ± 6*** | 75 ± 12** | 22 ± 2* |
| + Clenbuterol 2 ppm | 1.49 ± .22*** | 0.97 ± .11*** | 0.28 ± .04*** |
| | 96 ± 8*** | 79 ± 7*** | 18 ± 2** |

[1]Upper row: - weight of adipose tissue (average ± standard error, g)
[2]Lower row: - number of adipocytes (average ± standard error, DNA, μg/adipose tissue)
Significant difference: *p < 10%, p < 5%, *p < 1%

The cell number in adipose tissues shown in Table 7 represent the values including adipocytes, preadipocytes, fibroblasts, blood vessel cells, etc. The cells in the subcutaneous adipose tissue were investigated in detail as sorted into matured adipocytes, immatured adipocytes, and interstitial cells (stroma).

It is clearly noted from Table 8 showing the results of the investigation that particularly the differentiation of fibroblasts in the group of interstitial cells represented as stromas to preadipocytes was repressed.

TABLE 8

Effect of globin proteolysate on distribution of adipose tissue cells

| Treatment | Stroma | Preadipoytes | Adipocyte |
|---|---|---|---|
| Ordinary feed | 61 | 17 | 27 |
| 50% fat feed | 61 | 76 | 76 |
| +2% globin proteolysate | 37 | 58 | 47 |
| +4% globin proteolysate | 43 | 48 | 42 |
| +8% globin proteolysate | 48 | 37 | 47 |
| +12% globin proteolysate | 41 | 24 | 38 |
| + Clenbuterol 2 ppm | 36 | 30 | 30 |

These results suggest that the globin proteolysate repressed the differentiation of fibroblasts to such fat-storing cells as preadipocytes and adipocytes and that, owing to this effect, not only the adipocyte differentiation inhibiting peptide but also the globin proteolysate manifested usefulness in the prevention and therapy of obesity and cardiovascular diseases attendant on obesity.

[Test 5] Test for safety of the peptide of the invention

The peptides of the invention, Val-Tyr-Pro and Val-Thr-Leu, were orally administered at a dose of not less than 10 g/kg body weight (largest ingestable amount), with the ratio of the two peptides varied (0:1, 1:1, and 1:0) to male and female ICR mice. None of the mice suffered death.

Brief Description of the Drawings FIG. 1 is a diagram showing a gel chromatogram of a globin proteolysate. FIG. 2 is a diagram showing a reversed-phase (acid) chromatogram in Example 3, and FIG. 3 is a diagram showing a reversed-phase (neutral) chromatogram in Example 3.

Industrial applicability

This invention provides a novel adipocyte differentiation inhibiting peptide, adipocyte differentiation inhibiting agent containing the peptide as an active component, a specific health food (so-called physiologically functional food) having the function of inhibiting adipocyte differentiation, and a feed having the function of inhibiting adipocyte differentiation. It further provides a specific health food having the function of inhibiting adipocyte differentiation and a feed having the function of inhibiting adipocyte differentiation, both incorporating therein a proteolysate containing the adipocyte differentiation inhibiting peptide mentioned above. This invention permits prevention and therapy of obesity and cardiovascular diseases attendant on obesity such as hypertension and arteriosclerosis. It also allows improvement of the meat quality in domestic animals and culured fish.

We claim:

1. A pharmaceutical composition suitable for inhibiting adipocyte differentiation, comprising:

a) an effective amount of an adipocyte differentiation inhibiting peptide having an amino acid sequence of Val-Thr-Leu; and b) a pharmaceutically acceptable carrier.

2. The pharmaceutical composition of claim 1, wherein said pharmaceutical acceptable carrier comprises fillers, extenders, binders, moisturizing agents, disintegrating agents or surface active agents.

3. The pharmaceutical composition of claim 1, which is in a form of tablets, powder, granules, pills, solutions, suspensions or emulsions.

4. The pharmaceutical composition of claim 1, wherein said peptide is contained therein in an amount of from about 0.001 to 80% by weight.

5. A method of inhibiting adipocyte differentiation, comprising administering to a subject an amount of the pharmaceutical composition of claim 1 effective to inhibit adipocyte differentiation.

6. A food composition suitable for inhibiting adipocyte differentiation, which comprises:
   a) an effective amount of an adipocyte differentiation inhibiting peptide having an amino acid sequence of Val-Tyr-Pro or Val-Thr-Leu; and
   b) a food.

7. The food composition of claim 6, further comprising fillers, extenders, binders, moisturizing agents, disintegrating agents or surface active agents.

8. The food composition of claim 6, which is in a form of tablets, powder, granules, pills, solutions, suspensions or emulsions.

9. The food composition of claim 6, wherein said peptide is contained therein in an amount of from about 0.001 to 80% by weight.

10. The food composition of claim 6, wherein said food is milk, pudding, curry, hash, stew, meat sauce, ham, cake or chocolate.

11. A method of inhibiting adipocyte differentiation, comprising administering to a subject an amount of the food composition of claim 6 effective to inhibit adipocyte differentiation.

12. A feed composition suitable for inhibiting adipocyte differentiation, which comprises:
   a) an effective amount of an adipocyte differentiation inhibiting peptide having an amino acid sequence of Val-Tyr-Pro or Val-Thr-Leu; and
   b) a feed.

13. The feed composition of claim 12, further comprising fillers, extenders, binders, moisturizing agents, disintegrating agents or surface active agents.

14. The feed composition of claim 12, which is in a form of tablets, powder, granules, pills, solutions, suspensions or emulsions.

15. The feed composition of claim 12, wherein said peptide is contained therein in an amount of from about 0.1 to 4% by weight.

16. The feed composition of claim 12, which is for a domesticated animal.

17. The feed composition of claim 16, wherein said domesticated animal is selected from the group consisting of cows, hogs and chickens.

18. The feed composition of claim 12, which is for cultured fish.

19. A method of inhibiting adipocyte differentiation, comprising administering to a subject an amount of the feed composition of claim 12 effective to inhibit adipocyte differentiation.

20. A food composition suitable for inhibiting adipocyte differentiation, which comprises:
   a) an effective amount of a proteolysate containing not less than 0.1% by weight of an adipocyte differentiation inhibiting peptide having an amino acid sequence of Val-Tyr-Pro or Val-Thr-Leu; and
   b) a food.

21. The food composition of claim 20, further comprising fillers, extenders, binders, moisturizing agents, disintegrating agents or surface active agents.

22. The food composition of claim 20, which is in a form of tablets, powder, granules, pills, solutions, suspensions or emulsions.

23. The food composition of claim 20, wherein said peptide is contained in an amount of from about 0.001 to 80% by weight.

24. The food composition of claim 20, wherein said food is milk, pudding, curry, hash, stew, meat sauce, ham, cake or chocolate.

25. A method of inhibiting adipocyte differentiation, comprising administering to a subject an amount of the food composition of claim 20 effective to inhibit adipocyte differentiation.

26. A feed composition suitable for inhibiting adipocyte differentiation, which comprises:
   a) an effective amount of a proteolysate containing not less than 0.1% by weight of an adipocyte differentiation inhibiting peptide having an amino acid sequence of Val-Tyr-Pro or Val-Thr-Leu; and
   b) a feed.

27. The feed composition of claim 26, further comprising fillers, extenders, binders, moisturizing agents, disintegrating agents or surface active agents.

28. The feed composition of claim 26, which is in a form of tablets, powder, granules, pills, solutions, suspensions or emulsions.

29. The feed composition of claim 26, wherein said peptide is contained in an amount of from about 0.1 to 4% by weight.

30. The feed composition of claim 26, which is for a domesticated animal.

31. The feed composition of claim 30, wherein said domesticated animal is selected from the group consisting of cows, hogs and chickens.

32. The feed composition of claim 26, which is for cultured fish.

33. A method of inhibiting adipocyte differentiation, comprising administering to a subject an amount of the feed composition of claim 26 effective to inhibit adipocyte differentiation.

34. A method of inhibiting adipocyte differentiation, comprising administering to a subject an amount of an adipocyte differentiation inhibiting peptide having an amino acid sequence of Val-Tyr-Pro or Val-Thr-Leu effective to inhibit adipocyte differentiation.

* * * * *